(12) United States Patent
Meisel et al.

(10) Patent No.: US 6,986,901 B2
(45) Date of Patent: Jan. 17, 2006

(54) GASTROINTESTINAL COMPOSITIONS

(75) Inventors: Gerard M. Meisel, Budd Lake, NJ (US); Arthur A. Ciociola, Far Hills, NJ (US)

(73) Assignee: Warner-Lambert Company LLC, Morris Plains, NJ (US)

(*) Notice: Subject to any disclaimer, the term of this patent is extended or adjusted under 35 U.S.C. 154(b) by 234 days.

(21) Appl. No.: 10/196,053

(22) Filed: Jul. 15, 2002

(65) Prior Publication Data

US 2004/0013741 A1 Jan. 22, 2004

(51) Int. Cl.
- *A61F 13/00* (2006.01)
- *A61F 6/06* (2006.01)
- *A61F 9/02* (2006.01)
- *A61K 9/48* (2006.01)

(52) U.S. Cl. .................. 424/436; 424/422; 424/430; 424/433; 424/451; 424/464; 424/489

(58) Field of Classification Search ................ 424/422, 424/430, 433, 436, 451, 464, 489, 435, 439
See application file for complete search history.

(56) References Cited

U.S. PATENT DOCUMENTS

| | | | |
|---|---|---|---|
| 3,158,538 A | | 11/1964 | Lee |
| 3,257,275 A | | 6/1966 | Weisberg et al. |
| 4,301,163 A | * | 11/1981 | Torossian et al. ........... 514/357 |
| 4,462,982 A | | 7/1984 | Samejima et al. |
| 4,681,755 A | | 7/1987 | Colombo et al. |
| 5,143,728 A | * | 9/1992 | Cappel et al. .............. 424/738 |
| 5,245,080 A | | 9/1993 | Aubard et al. |
| 5,486,160 A | | 1/1996 | Rossi et al. |
| 5,498,422 A | | 3/1996 | Nakamichi et al. |
| 5,516,524 A | * | 5/1996 | Kais et al. ................... 424/439 |
| 5,574,054 A | | 11/1996 | Kitagawa et al. |
| 5,614,536 A | | 3/1997 | Monti et al. |
| 5,656,286 A | | 8/1997 | Miranda et al. |
| 5,658,888 A | | 8/1997 | Koga et al. |
| 5,686,494 A | | 11/1997 | Asano et al. |
| 5,693,337 A | | 12/1997 | Suzuki et al. |
| 5,700,410 A | | 12/1997 | Nakamichi et al. |
| 5,719,197 A | | 2/1998 | Kanios et al. |
| 5,776,495 A | | 7/1998 | Duclos et al. |
| 5,811,547 A | | 9/1998 | Nakamichi et al. |
| 5,837,285 A | | 11/1998 | Nakamichi et al. |
| 5,919,760 A | | 7/1999 | Simon |
| 5,980,882 A | | 11/1999 | Eichman |
| 5,981,557 A | | 11/1999 | Nagasawa et al. |
| 6,024,976 A | | 2/2000 | Miranda et al. |
| 6,027,747 A | | 2/2000 | Terracol et al. |
| 6,090,412 A | | 7/2000 | Hashimoto et al. |
| 6,121,301 A | | 9/2000 | Nagasawa et al. |
| 6,127,418 A | | 10/2000 | Bueno et al. |
| 6,156,771 A | | 12/2000 | Rubin et al. |

FOREIGN PATENT DOCUMENTS

| | | |
|---|---|---|
| CA | 967977 | 5/1975 |
| CA | 2136164 | 3/1995 |
| CN | 1092314 | 3/1993 |
| CN | 1118267 | 5/1994 |
| DE | 9859499 | 12/1998 |
| EP | 0 465 234 A1 * | 1/1992 |
| EP | 857482 | 2/1997 |
| FR | 2244469 | 8/1973 |
| FR | 4506 | 8/1993 |
| FR | 2771009 | 11/1997 |
| JP | 56128719 | 3/1980 |
| JP | 3066627 | 8/1989 |
| JP | 9052829 | 6/1995 |
| WO | WO 9501803 A1 * | 1/1995 |
| WO | WO 9725979 | 1/1996 |
| WO | WO 0076500 | 12/2000 |
| WO | WO 0121601 | 3/2001 |
| ZA | 6101840 | 8/1993 |

OTHER PUBLICATIONS

JW Read, JL Abitbol, KD Bardhan, PJ Whorwell, B Fraitag—"Efficacy and safety of the peripheral kappa agonist fedotozine versus placebo in the treatment of functional dyspepsia [see comments]," Gut Nov., 1997 41(5):664–8.

M Delvaux, D Louvel, E Lagier, B Scherrer, JL Abitbol, J Frexinos—"The kappa agonist fedotozine relieves hypersensitivity to colonic distention in patients with irritable bowel syndrome." Gastroenetrology, Jan.; 1999 116(1):38–45.

HD Allescher HD, S Ahmad, M Classen, EE Daniel—"Interaction of trimebutine and Jo–1196 (fedotozine) with opioid receptors in the canine ileum." J Pharmacol Exp Ther 257:836–42, May 1991.

T. Kamiya et al., "Effects of trimebutine maleate on gastric motility in patients with gastric ulcer", Journal of Gastroenterology, vol. 33, No. 6, Dec. 1998, pp. 823–827.

J. Kountouras MD, et al., "Efficacy of Trimebutine Therapy in Patients with Gastroesophageal Reflux Disease and Irritable Bowel Syndrome", Hepato–Gastroenterology Jan. 2002; vol. 49, 193–197.

* cited by examiner

*Primary Examiner*—Thurman K. Page
*Assistant Examiner*—S. Tran
(74) *Attorney, Agent, or Firm*—Linda A. Vag

(57) ABSTRACT

The invention relates to compositions and methods for treating and/or preventing lower gastrointestinal (GI) disorders in mammalian patients, more particularly for alleviating and/or preventing the lower GI symptoms associated with such disorders.

18 Claims, No Drawings

GASTROINTESTINAL COMPOSITIONS

This Continuation-In-Part application claims priority to the utility application filed on Jul. 10, 2002 by Express Mail No. EL819323530US.

FIELD OF THE INVENTION

The invention relates to compositions and methods for treating and/or preventing lower gastrointestinal (GI) disorders in mammalian patients, more particularly for alleviating and/or preventing the lower GI symptoms associated with such disorders.

BACKGROUND OF THE INVENTION

The primary function of the gastrointestinal tract is the absorption of ingested nutrients. This is achieved when transit along the esophagus and gastrointestinal tract is at a rate which facilitates optimal digestion and absorption of water and electrolytes. abnormal patterns in gastrointestinal motility result in number of disorders ranging from diffuse esophageal spasm (an esophageal obstructive disorder characterized by dysphagia), achalasia (an obstructive disorder in which the lower esophageal sphincter fails to relax adequately resulting in dysphagia) and noncardiac chest pain to functional bowel disorders such as the irritable bowel syndrome (IBS), non-ulcer dyspepsia, and idiopathic constipation.

IBS is particularly disturbing since it involves chronic episodes of diarrhea and/or constipation for which there is no identifiable organic cause. The disorder appears to result from faulty regulation in both the gastrointestinal and nervous systems.

Where drug therapy is indicated, the therapy includes prokinetic agents for constipation; anticholinergics, antispasmodics such as trimebutine, tricylic and serotonin reuptake inhibitor antidepressants, and sedatives for cramping pain; and opiates (such as loperamide and diphenoxylate) and cholestyramine for diarrhea. However, such therapy has proven to have limited, if any, efficacy.

Clearly, therefore, a significant unmet need remains for an efficacious and comprehensive treatment of patients afflicted with such lower GI disorders, including alleviation of such lower GI symptoms as chronic diarrhea, constipation and cramps.

The present inventors have found that gastrointestinal compositions comprising a gamma-aminobutyric acid analogs in combination with select gastrointestinal actives provide a more comprehensive reduction in IBS symptoms as compared to previous drug therapies.

Accordingly, an aspect of the present invention is to provide gastrointestinal compositions.

Another aspect of the present invention is to provide gastrointestinal compositions which prevent, reduce or alleviate the symptoms associated with IBS.

A further aspect of the present invention is to provide gastrointestinal compositions comprising amino-ether and/or ester oxides in combination with gastrointestinal actives selected from the group consisting of laxatives, antidiarrheals, antibiotics, antiulceratives, gastric secretion inhibitors, peristalitc stimulants, serotonin ($5HT_3$) receptor antagonists, serotonin ($5HT_4$) receptor agonists, selective serotonin reuptake inhibitor and mixtures thereof.

SUMMARY OF THE INVENTION

The present invention relates to compositions for treating or preventing gastrointestinal disorders, comprising:

a.) an amino-ether and/or -ester oxide having the formula:

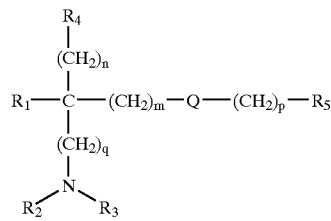

in which: $R_1$ is a lower alkyl, $R_2$ and $R_3$ which are the same or different are hydrogen or lower alkyl, $R_4$ is a phenyl or phenoxy nucleus optionally monosubstituted to trisubstituted by substituents which are identical or different, halogen or lower alkoxy, $R_5$ is a phenyl radical optionally monosubstituted to trisubstituted by substituents which are the same or different, halogen, lower alkyl, lower alkoxy or nitro, a pyridyl radical or a lower alkyl radical, Q is —O— or —COO—, n is equal to zero, 1 or 2, m and q are, independently of one another, equal to zero or to 1, p is an integer ranging from 0 to 9; and b.) a gastrointestinal active selected from the group consisting of laxatives, antidiarrheals, antibiotics, antiulceratives, gastric secretion inhibitors, peristalitc stimulants, serotonin ($5HT_3$) receptor antagonists, serotonin ($5HT_4$) receptor agonists, selective serotonin reuptake inhibitor and mixtures thereof.

Methods of treating or preventing gastrointestinal disorders using the above compositions are also disclosed.

DETAILED DESCRIPTION OF THE INVENTION

All percentages and ratios used herein are by weight of the total composition and all measurements made are at 25.degree. C., unless otherwise designated.

The compositions of the present invention can comprise, consist essentially of, or consist of, the essential as well as optional ingredients and components described herein. As used herein, "consisting essentially of" means that the composition or component may include additional ingredients, but only if the additional ingredients do not materially alter the basic and novel characteristics of the claimed compositions or methods.

All publications cited herein are hereby incorporated by reference in their entirety.

As used herein, a "pharmaceutically acceptable" component is one that is suitable for use with humans and/or animals without undue adverse side effects (such as toxicity, irritation, and allergic response) commensurate with a reasonable benefit/risk ratio.

By "safe and effective amount" is meant an amount of a compound or composition which is high enough to positively modify the condition being treated, but low enough to avoid serious side effects at a reasonable benefit/risk ratio within the scope of sound medical judgement. The safe and effective amount may vary with the age and physical condition of the person being treated, the severity of the condition, the specific ingredients employed, and like factors.

The phrase "gastrointestinal disorder", as used herein, means a disorder of the gastrointestinal tract, including the small and large intestines and the rectum, and/or symptoms usually attributed to a dysfunction of one or more of these organs, such as diarrhea, constipation and/or abdominal and lower abdominal cramping or pain. It is understood that gastro intestinal disorders include both disorders for which an organic cause (e.g. infection by a parasite) is known and disorders for which no organic cause can be ascertained, such as IBS. Gastrointestinal disorders, therefore, include, but are not limited to, irritable bowel syndrome, functional diarrhea, ulcerative colitis, collagenous colitis, microscopic colitis, lymphocytic colitis, inflammatory bowel disease, Crohn's disease, and infectious diarrhea such as diarrhea associated with amebiasis, giardiasis, a viral infection, cytomegalovirus infection, or a pathogenic bacterial infection. The bacterial infection may, for example, be an infection by a bacterium selected from the group consisting of a bacterium of the genus Escherichia, an *Escherichia coli* 0157:H7 bacterium, a bacterium of the genus Salmonella, a bacterium of the genus Shigella, a bacterium of the genus Campylobacter, a bacterium of the species *Campylobacter jejuni*, and a bacterium of the genus Yersinia The gastrointestinal compositions of the present invention, including the essential and optional components thereof, are described in detail hereinafter.

Essential Ingredients
Amino-Ether and/or Ester Oxides

The compositions and methods of the present invention comprise a safe and effective amount of an amino-ether and/or -ester oxide. Amino-ether and/or -ester oxides according to the invention conform to the formula:

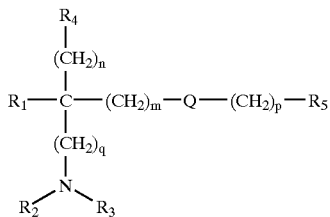

in which: $R_1$ is a lower alkyl, $R_2$ and $R_3$ which are the same or different are hydrogen or lower alkyl, $R_4$ is a phenyl or phenoxy nucleus optionally monosubstituted to trisubstituted by substituents which are identical or different, halogen or lower alkoxy, $R_5$ is a phenyl radical optionally monosubstituted to trisubstituted by substituents which are the same or different, halogen, lower alkyl, lower alkoxy or nitro, a pyridyl radical or a lower alkyl radical, Q is —O— or —COO—, n is equal to zero, 1 or 2, m and q are, independently of one another, equal to zero or to 1, p is an integer ranging from 0 to 9.

By lower radical are meant radicals having from 1 to 10 carbon atoms, preferably 1 to 6 carbon atoms, especially 1 to 4 carbon atoms in a straight or branched chain.

If $R_5$ is alkyl, it is preferably methyl. If the amino-ether oxides are halogenated, they are preferably brominated or chlorinated.

The invention also embraces the acid addition salts of amino-ether oxides, notably those of mineral acids, such as halohydrates, sulphates, phosphates, or organic acids such as maleates, citrates, malates, tartrates, methanesulphonates, camphosulphonates, benzoates, etc.

The invention further covers both racemic and optionally active forms which can be separated, particularly by forming salts with optically active acids.

Examples of suitable amino-ether and/or -ester oxides include trimebutine (3,4,5-trimethoxybenzoic acid 2-(dimethylamino)-2-phenylbutyl ester), fedozine ((R)-α-ethyl-N,N-dimethyl-α-[[(3,4,5-trimethoxyphenyl)methoxy]methyl] benenemethanamine) and mixtures thereof.

Trimebutine is available under the tradenames Modulon (Canada), Debridat (Italy), Cerekinon (Japan), and Polibutin (Spain). A more detailed description of Fedotozine can be found in U.S. Pat. No. 4,301,163 to Torossian et al. (1981) and U.S. Pat. No. 5,245,080 to Aubard et al. (1993), both of which are herein incorporated by reference in their entirety.

Fedotozine has been administered effectively at dosages of up to 210 mg daily, preferably 30 to 70 mg three times daily, and up to 100 mg intravenously daily. Trimebutine has been effectively administered orally at up to 600 mg/day, preferably up to 200 milligrams 3 times daily, or intramuscularly/intravenously at up to 100 milligrams every 12 hours. While mindful of individual patient parameters and symptom severity, the amino-ether and/or ester oxides are preferably administered orally at 1–75 mg/kg, preferably 2–50 mg/kg and most preferably at 5–20 mg/kg.

Gastrointestinal Actives

The compositions also comprise a safe and effective amount of a gastrointestinal active. In one embodiment the gastrointestinal active is selected from the group consisting of laxatives, antidiarrheals, antibiotics, antiulceratives, gastric secretion inhibitors, peristalitc stimulants, (5HT$_3$) receptor antagonists, serotonin (5HT$_4$) receptor agonists, selective serotonin reuptake inhibitors and mixtures thereof.

Suitable gastrointestinal actives include, but are not limited to, the following:

Laxatives

A safe and effective amount of a laxative may be added to the compositions of the subject invention. The exact amount of laxative to be used in the compositions will depend on the particular laxative utilized since such agents vary widely in potency. A more complete description of the various laxatives, including acceptable laxative effective amounts thereof for use in unit dose compositions of the present invention can be found in U.S. Pat. No. 5,516,524; herein incorporated by reference in its entirety; as well as the Handbook of Nonprescription Drugs, 12th Ed., Chapter 12, pp. 279–290 (American Pharmaceutical Association, Washington, D.C.; 2000); and Drug Facts and Comparisons (54th Ed. 2000), pp. 1166–1177; the cited pages of which are herein incorporated by reference.

Laxatives useful herein include, but are not limited to, hydrophilic derivatives of cellulose (such methylcellulose and carboxymethylcellulose sodium), malt soup extract, polyacrylic resins (preferably hydrophilic forms such as polycarbophil and calcium polycarbophil), plantago seeds, psyllium husk, dioctyl calcium sulfosuccinate, dioctyl potassium sulfosuccinate, dioctyl sodium sulfosuccinate, mineral oil, magnesium citrate, magnesium hydroxide, magnesium sulfate, dibasic sodium phosphate, monobasic sodium phosphate, sodium biphosphate, glycerin, anthraquinones or anthracene laxatives (such as aloe, cascara sagrada, danthron, senna, aloin, casanthranol, frangula, and rhubarb), diphenylmethanes (such as bisacodyl and phenolphthalein), and castor oil. Mixtures of the above laxatives can also be used.

Antidiarrheals

A safe and effective amount of an antidiarrheal may be added to the compositions of the subject invention. The exact amount of the antidiarrheal to be used in the compositions will depend on the particular antidiarrheal utilized since such agents vary widely in potency. A more complete description of the various antidiarrheals, including acceptable antidiarrheal effective amounts thereof for use in unit dose compositions of the present invention can be found in the Handbook of Nonprescription Drugs, 12th Ed., Chapter 13, pp. 312–316 (American Pharmaceutical Association, Washington, D.C.; 2000); and Drug Facts and Comparisons (54th Ed. 2000), pp. 1178–1182; the cited pages of which are herein incorporated by reference.

Antidiarrheals useful herein include, but are not limited to, natural or synthetic opiates (such as difenoxin, diphenoxylate, pargoric, opium tincture, and loperamide), anticholinergics (such as belladonna alkoloids-atropine hyoscyamine, and hyosine), acetyltannic acid, albumin tannate, alkofanone, aluminum salicylates, catechin, lidamidine, mebiquine, trillium, and uzarin. Mixtures of the above antidiarrheals can also be used.

Antiulcerative

A safe and effective amount of an antiulcerative may be added to the compositions of the subject invention. The exact amount of the antiulcerative to be used in the compositions will depend on the particular antiulcerative utilized since such agents vary widely in potency. A more complete description of the various antiulceratives, including acceptable antiulcerative effective amounts thereof for use in unit dose compositions of the present invention can be found in the Drug Facts and Comparisons (54th Ed. 2000), pp. 1131–1139; the cited pages of which are herein incorporated by reference.

Antiulcerative useful in the present invention include, but are not limited to, aceglutamide aluminum complex, $\epsilon$-acetamidocaproic acid zinc salt, acetoxolone, arbaprostil, benexate hydrochloride, bismuth subcitrate sol (dried), carbenoxolone, cetraxate, cimetidine, enprostil, esaprazole, famotidine, ftaxilide, gefarnate, guaiazulene, irsogladine, nizatidine, omeprazole, ornoprostil, $\gamma$-oryzanol, pifarnine, pirenzepine, plaunotol, ranitidine, rioprostil, rosaprostol, rotraxate, roxatidine acetate, sofalcone, spizofurone, sucralfate, teprenone, trimoprostil, thrithiozine, troxipide, and zolimidine. Mixtures of the above antiulcerative can also be used.

Antibiotics

A safe and effective amount of an antibiotic may be added. The exact amount of antibiotic to be used in the compositions will depend on the particular antibiotic utilized since such agents vary widely in potency.

A wide variety of antibiotics may be used according to the invention, including for example nitroimidazole antibiotics (e.g. tinidazole or metronidazole), tetracyclines (e.g. tetracyclin, doxycyclin and minocyclin), pencillins (e.g. amoxycillin, ampicillin and mezlocillin), cephalosporins (e.g. cefachlor, cefadroxil, cephradine, cefuroxime, cefuroxime axetil, cephalexin, cefpodoxime proxetil, ceftazidime and ceftriaxone), carbopenems (e.g. imipenem and meropenem), amino-glycosides (e.g. paromonycin), macrolide antibiotics (e.g. erythromycin, clarithromycin and azithromycin), lincosamide antibiotics (e.g. clindamycin), 4-quinolones (e.g. ofloxacin, ciprofloxacin, pefloxacin and norfloxacin), rifamycins (e.g. rifampicin), nitrofurantoin and derivatives of 10-(1-hydroxyethyl)-11-oxo-1-azatricyclo [7.2.0.0.3.8]undec-2-ene-2-carboxylic acid and mixtures thereof as well as those described in U.S. Pat. No. 5,719,197 to Kanios et al. (1998), published European Patent Specification No. 0416953 and published International Patent Specification No. WO92/03437, each of which are herein incorporated by reference in its entirety.

Mixtures of any of the above-mentioned antibiotic compounds can also be used.

Gastric Secretion Inhibitors

A safe and effective amount of a gastric secretion inhibitor may be added to the compositions of the subject invention. Suitable gastric secretion inhibitors include, but are not limited to, enterogastrone and octreotide. The exact amount of gastric secretion inhibitors to be used in the compositions will depend on the particular gastric secretion inhibitor utilized since such agents vary widely in potency. A more complete description of the various Gastric Secretion Inhibitors, including acceptable e Gastric Secretion Inhibitor effective amounts thereof for use in unit dose compositions of the present invention can be found in the Drug Facts and Comparisons (54th Ed. 2000), pp. 352–354; the cited pages of which are herein incorporated by reference. Mixtures of the above gastric secretion inhibitors can also be used.

Peristaltic Stimulants

A safe and effective amount of a peristaltic stimulant may be added to the compositions of the subject invention. Suitable peristaltic stimulants include, but are not limited to, dexpanthenol, metoclopromide, cisapride, and domperidone. The exact amount of peristalitc stimulants to be used in the compositions will depend on the particular peristalitc stimulant utilized since such agents vary widely in potency. A more complete description of the various, Peristaltic Stimulants including acceptable Peristaltic Stimulant effective amounts thereof for use in unit dose compositions of the present invention can be found in the Drug Facts and Comparisons (54th Ed. 2000), pp. 1188–1193; the cited pages of which are herein incorporated by reference. Mixtures of the above peristalitc stimulants can also be used.

Serotonin ($5HT_3$) Receptor Antagonist

A safe and effective amount of a serotonin ($5HT_3$) receptor antagonist may be added to the compositions of the subject invention. Suitable serotonin ($5HT_3$) receptor antagonists include, but are not limited to, cilansetron, dolasetron, ondansetron, alosetron and mixtures thereof. The exact amount of serotonin ($5HT_3$) receptor antagonists to be used in the compositions will depend on the particular serotonin ($5HT_3$) receptor antagonist utilized since such agents vary widely in potency. A more complete description of the various serotonin ($5HT_3$) receptor antagonists, including acceptable effective amounts thereof for use in unit dose compositions of the present invention can be found in U.S. Pat. No. 6,235,745, herein incorporated by reference and the Drug Facts and Comparisons (54th Ed. 2000), pp. 869–872 and KU47; the cited pages of which are herein incorporated by reference. Mixtures of the above serotonin ($5HT_3$) receptor antagonists can also be used.

Serotonin ($5HT_4$) Receptor Agonist

A safe and effective amount of a serotonin ($5HT_4$) receptor agonist may be added to the compositions of the subject invention. Suitable serotonin ($5HT_4$) receptor agonists include, but are not limited to tegaserod, renzapride and prucalopride. The exact amount of serotonin ($5HT_4$) receptor agonists to be used in the compositions will depend on the particular serotonin ($5HT_4$) receptor agonist utilized since such agents vary widely in potency. Tegaserod is a partial serotonin ($5HT_4$) receptor agonist which accelerates orocecal transit (without effect on gastic emptying) and tends to enhance colonic transit. 12 mg/day of tegaserod is taught to result in effective relief of irritable bowel syndrome symptoms. Prucalopride is a full serotonin ($5HT_4$) receptor agonist which accelerates gastric, small bowel and colonic transit in functional constipation. Up to 4 mg/day, particularly 2–4 mg/day, of prucalopride is taught to result in effective relief of untoward bowel symptoms. Renzapride possesses both serotonin ($5HT_4$) receptor agonist and serotonin ($5HT_3$) receptor antagonist activity, providing increased gastric emptying and reduced gastrintestinal transit time. Mixtures of the above serotonin ($5HT_4$) receptor agonists can also be used.

Selective Serotonin Reuptake Inhibitors

A safe and effective amount of a selective serotonin reuptake inhibitor may be added to the compositions of the subject invention. Suitable selective serotonin reuptake inhibitors include, but are not limited to, fluoxetine, fluvoxamine, paroxetine, and sertraline. The exact amount of selective serotonin reuptake inhibitors to be used in the compositions will depend on the particular selective serotonin reuptake inhibitor utilized since such agents vary widely in potency. A more complete description of the various selective serotonin reuptake inhibitors, including acceptable effective amounts thereof for use in unit dose compositions of the present invention can be found in the Drug Facts and Comparisons (54th Ed. 2000), pp. 918–928; the cited pages of which are herein incorporated by reference. Mixtures of the above selective serotonin reuptake inhibitors can also be used.

Preferred for use herein as the gastrointestinal active are bulk forming laxatives such as methylcellulose, carboxymethylcellulose sodium, malt soup extract, hydrophilic polyacrylic resins, plantago seeds, psyllium husk and mixtures thereof. Most preferred for use herein are hydrophilic polyacrylic resins such as polycarbophil and/or calcium polycarbophil. Calcium polycarbophil is monographed and every unit contains 500 mg of polycarbophil (650 mg polycarbophil) with a dosing of 2 units(1 gm polycarbophil) up to 4 times a day and, preferably not to exceed 12 units (6 gm) in a 24 hour period.

Further dosage information concerning disclosed actives is summarized in the table below:

| Generic Name | Suitable Strengths and Dosage Forms (Brand Names) | Usual Adult Dosage |
| --- | --- | --- |
| Bulk-Foaming Laxatives | | |
| Calcium polycarbophil | 625-mg tablets that provide 500 mg of polycarbophil (Konsyl Fiber) | 1–6 g/day as polycarbophil in divided doses |
| Methylcellulose | 2 g/Tbsp oral powder (Citrucel) | 4–6 g/day in divided doses |
| Psyllium | 3.4 g/tsp or 3.4 g/Tbsp oral powder; 1.7 g wafer (Metamucil) | 2.5–30 g/day in divided doses |
| Antidiarrheals (opiate and anticholinergic agents) | | |
| Diphenoxylate | 2.5-mg tablets; 2.5 mg/5 mL oral liquid (Lomotil) | 2.5–5 mg four times daily as needed for diarrhea |
| Loperamide | 2-mg tablets and capsules; 1 mg/5 mL oral liquid (Imodium) | 2–4 mg up to four times daily as needed. |
| Dicyclomine | 10-mg capsules; 20-mg tablets; 10 mg/5 mL syrup (Bentyl) | 10–20 mg three or four times daily |
| Hyoscyamine | 0.125-mg tablets; 0.125 mg/mL; 0.125 mg/5 mL elixir (Levsin) | 0.15–0.3 mg up to four times daily |
| Tincture of bellonna | Tincture with 0.3 mg/mL alkaloids of belladonna leaf | 0.6–1 mL three or four times daily |
| Peristaltic Stimulants | | |
| Cisapride | 10-, 20-mg tablets; 5 mg/mL oral suspension (Propulsid) | 5–10 mg three times daily |
| Metoclopramide | 5-, 10-mg tablets; 5 mg/5 mL oral liquid | |
| Selective Serotonin Reuptake Inhibitors | | |
| Fluoxetine | 20-mg capsules; 20 mg/5 mL oral solution (Prozac) | |
| Fluvoxamine | 50-, 100-mg tablets (Luvox) | |
| Paroxetine | 10 mg/5 mL oral suspension; 10-, 20-, 30-, 40-mg tablets (Paxil) | |
| Sertraline | 25-, 50-, 100-mg tablets (Zoloft) | |
| Serotonin (5HT$_3$) Receptor Antagonist | | |
| Alosetron | 1-mg tablets (Lotronex) | 1 mg twice daily |
| Granisetron | 1-mg tablets (Kytril) | |
| Ondansetron | 4-, 8-mg tablets (Zofran) | 4 mg three times daily |
| Gastric Secretion Inhibitors | | |
| Octreotide | 50, 100, 200, 500, 1000 µg/mL sterile solution for s.c. or i.v. injection (Sandostatin); 10-, 20-, 30-mg sterile suspension for i.m. injection (Sandostatin LAR Depot) | |

CNS = central nervous system; GI = gastrointestinal; 5-HT3 = serotonin (5-hydroxytryptamine) receptor subtype 3; i.m. = intramuscular; i.v. = intravenous; s.c. = subcutaneous.

Optional Ingredients

A safe and effective amount of an anti-inflammatory agent may be added to the compositions of the subject invention. The exact amount of anti-inflammatory agent to be used in the compositions will depend on the particular anti-inflammatory agent utilized since such agents vary widely in potency. A more complete description of the various NSAID's, including acceptable analgesically effective amounts thereof for use in unit dose compositions of the present invention also appears in applicants co-pending U.S. application Ser. No. 474,358, filed Mar. 11, 1983, and now U.S. Pat. No. 4,486,436, and Ser. No. 578,288, filed Feb. 8, 1984, now U.S. Pat. No. 4,522,826 the entire disclosures of which are incorporated herein by reference.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. Mixtures of the above steroidal anti-inflammatory agents can also be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, reference may be had to standard texts, including Anti-inflammatory and Anti-Rheumatic Drugs, K. D. Rainsford, Vol. I–III, CRC Press, Boca Raton, (1985), and Anti-inflammatory Agents, Chemistry and Pharmacology 1, R. A. Scherrer, et al., Academic Press, New York (1974), each incorporated herein by reference.

Specific non-steroidal anti-inflammatory agents useful in the composition invention include, but are not limited to:

1) the oxicams, such as piroxicam, isoxicam, tenoxicam, sudoxicam, and CP-14,304;
2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and
6) the pyrazoles, such as phenylbutazone, oxyphenbutazone, feprazone, azapropazone, and trimethazone.

Mixtures of these non-steroidal anti-inflammatory agents may also be employed, as well as the pharmologically acceptable salts and esters of these agents. For example, etofenamate, a flufenamic acid derivative, is particularly useful for topical application. Of the nonsteroidal anti-inflammatory agents, ibuprofen, naproxen, flufenamic acid, etofenamate, aspirin, mefenamic acid, meclofenamic acid, piroxicam and felbinac are preferred; ibuprofen, naproxen, etofenamate, aspirin and flufenamic acid are most preferred.

Finally, so-called "natural" anti-inflammatory agents are useful in methods of the subject invention. Such agents may suitably be obtained as an extract by suitable physical and/or chemical isolation from natural sources (e.g., plants, fungi, by-products of microorganisms). For example, candelilla wax, alpha bisabolol, aloe vera, Manjistha (extracted from plants in the genus Rubia, particularly Rubia Cordifolia), and Guggal (extracted from plants in the genus Commiphora, particularly Commiphora Mukul), kola extract, chamomile, and sea whip extract, may be used. Additional anti-inflammatory agents useful herein include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$–$C_{24}$ saturated or unsaturated esters of the acids, preferably $C_{10}$–$C_{24}$, more preferably $C_{16}$–$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

Mixtures of any of the above anti-inflammatory agents can also be used.

Carriers

In accordance with the practices of the present invention, the gastrointestinal compositions may be administered in admixture with suitable pharmaceutical diluents, carriers or other excipients (collectively referred to as "carrier" materials) suitably selected with respect to the intended route of administration and conventional pharmaceutical practices. The gastrointestinal compositions of the present invention are typically mixed with a pharmaceutically acceptable carrier. This carrier can be a solid or liquid and the type is generally chosen based on the type of administration being used.

The actives can be coadministered in the form of a tablet or capsule, liposome, as an agglomerated powder or in a liquid form. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents.

Examples of suitable tablet or capsule form ingredients, include but are not limited, to oral non-toxic pharmaceutically acceptable inert carrier such as lactose, starch, sucrose, cellulose, magnesium stearate, dicalcium phosphate, calcium sulfate, mannitol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodiumbenzoate, sodium acetate, sodium chloride, etc. Disintegrators include, without limitation, starch, methylcellulose, agar, bentonite, guar gum, etc.

Of course, additionally, the compositions of the present invention may be formulated in sustained release form to provide the rate controlled release of any one or more of the components to optimize the therapeutic effects, i.e., analgesia, skeletal muscle relaxation, etc. while minimizing undesirable side effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Similarly, injectable dosage units may be utilized to accomplish intravenous, intramuscular or subcutaneous administration and, for such parenteral administration, suitable sterile aqueous or non-aqueous solutions or suspensions, optionally containing appropriate solutes to effectuate isotonicity, will be employed.

Specific examples of pharmaceutical acceptable carriers and excipients that may be used to formulate oral dosage forms of the present invention are described in U.S. Pat. No. 3,903,297 to Robert, issued Sep. 2, 1975, herein incorporated by reference in its entirety. Techniques and compositions for making dosage forms useful in the present invention are described in the following references: 7 Modern Pharmaceutics, Chapters 9 and 10 (Banker & Rhodes, Editors, 1979); Lieberman et al., Pharmaceutical Dosage Forms: Tablets (1981); and Ansel, Introduction to Pharmaceutical Dosage Forms 2nd Edition (1976), each of which are herein incorporated by reference in its entirety.

The gastrointestinal compositions of the present invention may also be formulated and administered by other methods known for administering gastrointestinal actives. For example, the composition may be adapted for topical administration in the form of rectal preparations such as a rectal cream, gel, ointment, or suppository.

Method of Treatment

The method of treatment can be any suitable method which is effective in the treatment of the particular type of lower gastrointestinal disorder that is being treated. Treatment may be oral, rectal, parenteral, intravenous administration or injection. The method of applying an effective amount also varies depending on the lower gastrointestinal disorder being treated. It is believed that oral treatment by tablet, capsule or liquid will be the preferred method of administering the compounds to warm blooded mammals.

The method of treating lower gastrointestinal disorders may also be by rectal, parenteral, or intravenous administration. The actual time and dosage will depend on the type of the lower gastrointestinal disorder being treated and the desired blood levels.

EXAMPLES

The compositions in the following illustrate specific embodiments of the gastrointestinal compositions of the present invention, but are not intended to be limiting thereof. Other modifications can be undertaken by the skilled artisan without departing from the spirit and scope of this invention.

All exemplified compositions can be prepared by conventional formulation and mixing techniques. Component amounts are listed as weight percents and exclude minor materials such as diluents, filler, and so forth. The listed formulations, therefore, comprise the listed components and any minor materials associated with such components.

Example I

The following is an example of an antidiarrheal capsule composition of the present invention. The capsule is formed by combining and mixing the ingredients of each column using conventional technology and transferring the mixture to an appropriate sized hard gelatin capsule for oral administration.

| Ingredient | %/w/w |
| --- | --- |
| Loperamide | 0.500 |
| Trimebutine | 50.000 |
| Corn Starch USP[1] | 27.000 |
| Talc USP[2] | 7.5 |
| Lactose Monohydrate NF[3] | 15.000 |

[1]Corn Starch Modified supplied by National Starch and Chemical Co.
[2]Supplied by Whittaker, Clark & Daniels, Inc.
[3]Supplied by Archer Daniel Midland Co.

Once mixed the ingredients are incoporated into #2 hard gelatin capsules composed of gelatin, titanium dioxide and colorant and administered orally.

Example II

The following is an example of a Trimebutine-laxative combination capsule composition of the present invention. The capsule is formed by combining and mixing the ingredients of each column using conventional technology and transferring the mixture to an appropriate sized hard gelatin capsule for oral administration.

| Ingredient | %/w/w |
| --- | --- |
| Trimebutine | 25.000 |
| Calcium Polycarbophil | 50.000 |
| Microcrystalline Cellulose NF[1] | 7.5 |
| Talc USP[2] | 6.25.000 |

[1]Available as Avicel 102 supplied by FMC Corporation
[2]Supplied by Whittaker, Clark & Daniels, Inc.

Once mixed the ingredients are incoporated into #2 hard gelatin capsules composed of gelatin, titanium dioxide and colorant and administered orally.

Example III

The following is an example of an antiulcerative tablet composition of the present invention.

| Ingredient | %/w/w |
| --- | --- |
| Trimebutine | 40.000 |
| Ranitidine HCL | 30.000 |
| Microcrystalline Cellulose | 24.40 |
| Lactose Monohydrate NF | 4.000 |
| Magnesium Stearate NF | 1.60 |

[1]Available as Avicel 102 supplied by FMC Corporation
[2]Supplied by Archer Daniel Midland Co.
[3]Magnesium Stearate (Light) supplied by Witco Corporation.

In a suitable vessel, the trimebutine, ranitidine HCL, microcrystalline cellulose and lactuose monohydrate are milled to a suitable size and mixed until homogeneous. The magnesium strearate is added and the mixture is mixed until homogeneous. The mixture is then discharged and compressed using conventional tablet tooling to a suitable hardness (e.g., 10–12 kp) to target a net table weight of 500 mg. The tablet is administered orally.

What is claimed is:

1. A composition for treating or gastrointestinal disorders, comprising:

a.) a safe and effective amount of an amino-ether and/or -ester oxide having the formula:

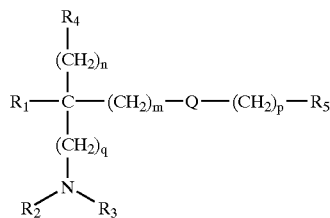

in which: $R_1$ is a lower alkyl, $R_2$ and $R_3$ which are the same or different are hydrogen or lower alkyl, $R_4$ is a phenyl or phenoxy nucleus optionally monosubstituted to trisubstituted by substituents which are identical or different, halogen or lower alkoxy, $R_5$ is a phenyl radical optionally monosubstituted to trisubstituted by substituents which are the same or different, halogen, lower alkyl, lower alkoxy or nitro, a pyridyl radical or a lower alkyl radical, Q is —O— or —COO—, n is equal to zero 1 or 2, m and q are, independently of one another, equal to zero or to 1, wherein the amino-ether and/or -ester oxide is selected from the group consisting of trimebutine, fedotozine and mixtures thereof; and b.) a safe and effective amount of a gastrointestinal active selected from the group consisting of laxatives, antidiarrheals, antibiotics, antiulceratives, gastric secretion inhibitors, peristalitc stimulants, serotonin (5HT$_3$) receptor antagonists, serotonin (5HT$_4$) receptor agonists, selective serotonin reuptake inhibitor and mixture thereof; and c.) an anti-inflammatory compound.

2. A composition according to claim 1, wherein the laxative is selected from the group consisting of methylcellulose, carboxymehylcellulose sodium, malt soup extract, polyacrylic resin, plantago seeds, dioctyl calcium sulfosuccinate, dioctyl potassium sulfosuccinate, dioctyl sodium sulfosuccinate, mineral oil, magnesium citrate, magnesium hydroxide, magnesium sulfate, dibasic sodium phosphate, monobasic sodium phosphate, sodium biphosphate, glycerin, anthraquinones, diphenylmethanes, castor oil and mixtures thereof.

3. A composition according to claim 1, wherein the antidiarrheal is selected from the group consisting of natural opiates, synthetic opiates, anticholinergics, acetyltannic acid, albumin tannate, alkofanone, aluminum salicylates, catechin, lidamidine, mebiquine, trillium, uzarin and mixtures thereof.

4. A composition according to claim 1, wherein the antiulcerative is selected from the group consisting of aceglutamide aluminum complex, ε-acetamidocaproic acid zinc salt, acetoxolone, arbaprostil, benexate hydrochloride, bismuth subcitrate sol (dried), carbenoxolone, cetraxate, cimetidine, enprostil, esaprazole, famotidine, ftaxilide, gefarnate, guaiazulene, irsogladine, nizatidine, omeprazole, omoprostil, γ-oryzanol, pifarnine, pirenzepine, plaunotol, ranitidine, rioprostil, rosaprostol, rotraxate, roxatidine acetate, sofalcone, spizofurone, sucralfate, teprenone, trimoprostil, thrithiozine, troxipide, zolimidine and mixtures thereof.

5. A composition according to claim 1, wherein the gastric secretion inhibitor is selected from the group consisting of enterogastrone, octreotide and mixtures thereof.

6. A composition according to claim 1, wherein the peristalitc stimulant is selected from the group consisting of metoclopromide, cisapride, domperidone and mixtures thereof.

7. A composition according to claim 1, wherein the serotonin (5HT$_3$) receptor antagonist is selected from the group consisting of renzapride cilansetron, ondansetron, alosetron and mixtures thereof.

8. A composition according to claim 1, wherein the serotonin (5HT$_4$) receptor agonist is selected from the group consisting of tegaserod, prucalopride and mixtures thereof.

9. A composition according to claim 1, wherein the selective serotonin reuptake inhibitor is selected from the group consisting of fluoxetine, fluvoxamine, paroxetine, sertraline and mixtures thereof.

10. A composition according to claim 1, wherein antibiotic is selected from the group consisting of nitroimidazole antibiotics, tetracyclines, pencillins, cephalosporins, carbopenems, amino-glycosides, macrolide antibiotics, lincosamide antibiotics, 4-quinolones, rifamycins, nitrofurantoin and derivatives of 10-(1-hydroxyethyl)-11-oxo-1-azatricyclo[7.2.0.0.3.8]undec-2-ene-2-carboxylic acid and mixtures thereof.

11. A composition according to claim 1, wherein the antiinflammatory compound is selected from the group consisting of corticosteroids, non-steroidal antiinflammatory compounds and mixtures thereof.

12. A composition according to claim 11, wherein the antiinflammatory compound is a non-steroidal antiinflammatory compound.

13. A composition according to claim 1, in the form of a tablet, capsule, microcapsule, suspension, solution, injectable, rectal suppository, rectal cream, rectal ointment, rectal gel.

14. A composition according to claim 1, wherein the gastrointestinal active is a laxative.

15. A composition according to claim 1, wherein the laxative is a bulk forming laxative.

16. A composition according to claim 1, wherein the laxative is selected from the group consisting of polycarbophil, calcium polycarbophil and mixtures thereof.

17. A composition for treating or gastrointestinal disorders according claim 1, comprising:

a.) a safe and effective amount of trimebutine, and b.) a safe and effective amount of polycarbophil.

18. A composition for treating or gastrointestinal disorders according claim 1, comprising:

a.) a safe and effective amount of fedotozine; and c.) a safe and effective amount of polycarbophil.

* * * * *